(12) United States Patent
Maier-Rosenkranz et al.

(10) Patent No.: US 8,470,173 B2
(45) Date of Patent: Jun. 25, 2013

(54) COLUMN PACKING APPARATUS AND METHOD OF MAKING AND USING THE SAME

(75) Inventors: Juergen Maier-Rosenkranz, Tubingen (DE); Jochen Saar, Frankenthal (DE); Oliver Genz, Staufen i. Br. (DE)

(73) Assignee: Alltech Associates, Inc., Columbia, MD (US)

( * ) Notice: Subject to any disclaimer, the term of this patent is extended or adjusted under 35 U.S.C. 154(b) by 239 days.

(21) Appl. No.: 12/918,977

(22) PCT Filed: Feb. 19, 2009

(86) PCT No.: PCT/US2009/001038
§ 371 (c)(1),
(2), (4) Date: Feb. 25, 2011

(87) PCT Pub. No.: WO2009/105216
PCT Pub. Date: Aug. 27, 2009

(65) Prior Publication Data
US 2012/0085462 A1    Apr. 12, 2012

Related U.S. Application Data

(60) Provisional application No. 61/066,613, filed on Feb. 21, 2008.

(51) Int. Cl.
*B01D 15/08* (2006.01)
(52) U.S. Cl.
USPC .................... 210/198.2; 210/656; 210/143

(58) Field of Classification Search
USPC ...... 210/635, 656, 143, 198.2, 502.1; 141/12, 141/80
See application file for complete search history.

(56) References Cited

U.S. PATENT DOCUMENTS

| | | | |
|---|---|---|---|
| 4,737,292 A | 4/1988 | Ritacco et al. | 210/656 |
| 4,891,133 A | 1/1990 | Colvin, Jr. | 210/198.2 |
| 5,169,522 A | 12/1992 | Shalon et al. | 210/198.2 |
| 5,213,683 A | 5/1993 | Mann | 210/198.2 |
| 5,462,659 A | 10/1995 | Saxena et al. | 210/198.2 |
| 5,667,675 A | 9/1997 | Hatch et al. | 210/198.2 |
| 5,866,008 A | 2/1999 | Shalon et al. | 210/656 |
| 5,893,971 A | 4/1999 | Shalon et al. | 210/198.2 |
| 6,001,260 A | 12/1999 | Hatch et al. | 210/656 |
| 6,036,855 A | 3/2000 | Shalon et al. | 210/198.2 |
| 6,074,556 A | 6/2000 | Van Davelaar | 210/198.2 |
| 6,090,278 A | 7/2000 | Lally et al. | 210/198.2 |
| 6,190,560 B1 | 2/2001 | Mann | 210/656 |
| 6,558,539 B1 | 5/2003 | Mann | 210/198.2 |
| 6,736,974 B1 | 5/2004 | Mann | 210/656 |
| 6,872,302 B2 | 3/2005 | Aste | 210/198.2 |
| 6,932,904 B2 | 8/2005 | Laub et al. | 210/198.2 |
| 7,008,532 B2 | 3/2006 | Shalon et al. | 210/198.2 |
| 7,132,053 B2 | 11/2006 | Hauck et al. | 210/656 |
| 7,238,282 B2 | 7/2007 | Perreault et al. | 210/198.2 |
| 8,163,177 B2 * | 4/2012 | Van Pelt | 210/198.2 |
| 2006/0219616 A1 | 10/2006 | Noyes et al. | 210/198.2 |

FOREIGN PATENT DOCUMENTS

| | | |
|---|---|---|
| EP | 171005 | 6/2008 |
| GB | 1074504 | 7/1967 |
| WO | 9732207 | 9/1997 |
| WO | 0051706 | 9/2000 |

* cited by examiner

*Primary Examiner* — Ernst G Therkorn
(74) *Attorney, Agent, or Firm* — William D. Bunch

(57) ABSTRACT

Column packing apparatus are disclosed. Methods of making and using column packing apparatus are also disclosed.

10 Claims, 11 Drawing Sheets

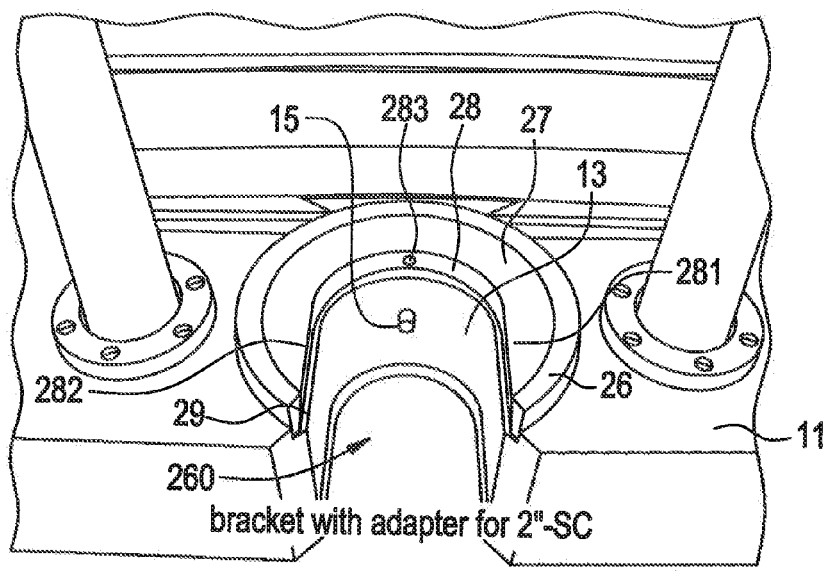
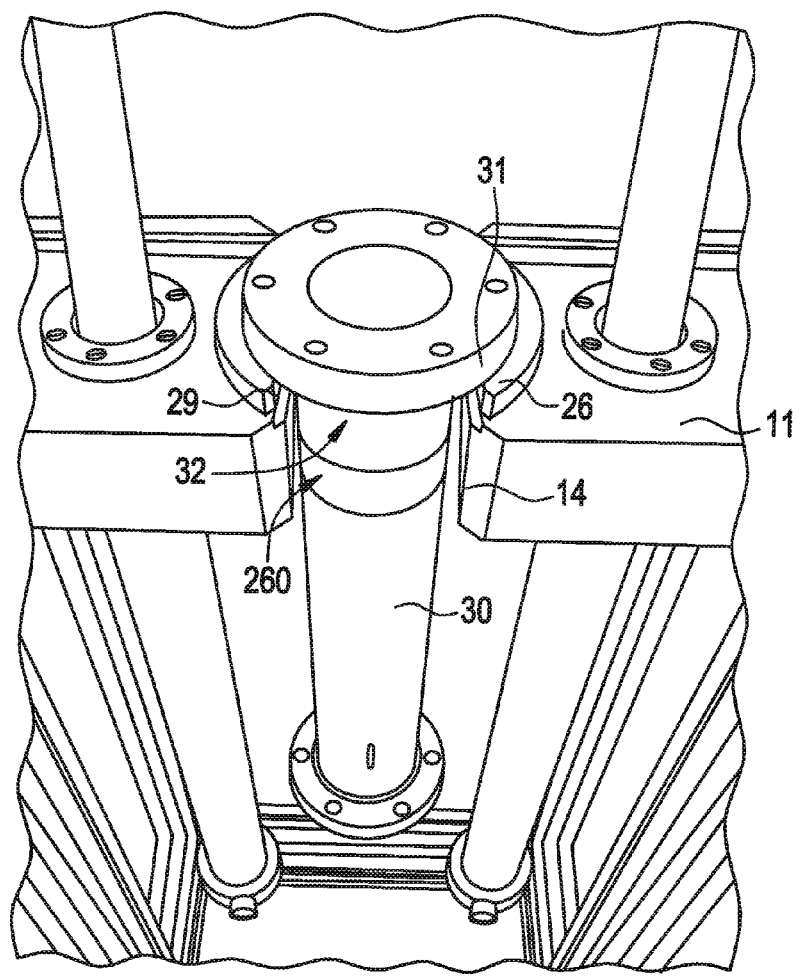

COLUMN PACKING APPARATUS AND METHOD OF MAKING AND USING THE SAME

CROSS REFERENCE TO RELATED APPLICATION

This application is a continuation of U.S. Patent Application Ser. No. 61/066,613 filed Feb. 21, 2008.

REFERENCE TO RELATED APPLICATIONS

This application is a 371 of PCT/US09/01038 filed Feb. 19, 2000.

FIELD OF THE INVENTION

The present invention is directed to column packing apparatus and methods of making and using column packing apparatus.

BACKGROUND OF THE INVENTION

There is a need in the art for a column packing apparatus that is capable of packing columns having different column dimensions, for example, a column having a 25 mm (1 inch) inner diameter and a column having a 50 mm (2 inches) inner diameter, and adjusting one or more packing parameters (e.g., packing pressure) based on the column dimensions.

SUMMARY OF THE INVENTION

The present invention addresses some of the difficulties and problems discussed above by the discovery of column packing apparatus capable of packing different sized columns, and automatically adjusting a packing pressure based on the size of the column being packed. The present invention also discloses apparatus components that can be used in column packing apparatus. The apparatus components may be used together within a given column packing apparatus or individually within a given column packing apparatus.

In one exemplary embodiment of the present invention, the column assembly comprises an adapter support member having an upper surface, a lower surface, at least one sidewall extending from the upper surface to the lower surface, and a column positioning slot within the adapter support member, wherein the column positioning slot comprises a slot mouth, and a portion of the at least one sidewall (of the adapter support member), the slot mouth having a slot mouth width that is sized to accommodate a largest column width; and a pin switch having a pin switch end that extends into (i) the column positioning slot or (ii) a volume of space directly below the column positioning slot, wherein the pin switch is operatively adapted to adjust a packing pressure of the column packing apparatus depending on a location of the pin switch end within (i) the column positioning slot or (ii) the volume of space directly below the column positioning slot. In this exemplary embodiment, a first column may not change the location of the pin switch end, while a second column does change the location of the pin switch end due to the dimensions of each column. Changing the location of the pin switch end initiates a signal from the pin switch to the column packing apparatus to apply a pressure for the second column that differs from a pressure applied when the pin switch end is in its initial position (i.e., when the first column is positioned within the column packing apparatus).

In another exemplary embodiment, the present invention relates to a column packing apparatus for packing columns of different size comprising a column compressing member for packing media in said column, a compressing member controller for controlling pressure exerted on the media during packing, and a column holding member, wherein the column holding member includes a sensor that determines the size of the column when the column is inserted into the holding member and that communicates with the controller.

In a further exemplary embodiment, the present invention relates to a column packing apparatus for packing columns with media comprising a column compressing member for packing the media, a compressing member controller for controlling pressure exerted on the media during packing, and a hydraulic system for generating the pressure, wherein the system includes a self degassing feature.

The present invention is also directed to methods of making column packing apparatus. In one exemplary method, the method of making a column packing apparatus comprises providing an adapter support member having an upper surface, a lower surface, at least one sidewall extending from the upper surface to the lower surface, and a column positioning slot within the adapter support member, wherein the column positioning slot comprises a slot mouth, and a portion of the at least one sidewall, and the slot mouth has a slot mouth width that is sized to accommodate a largest column width; providing a pin switch having a pin switch end, wherein the pin switch is operatively adapted to adjust a packing pressure of the column packing apparatus depending on a location of the pin switch end; and positioning the pin switch so that the pin switch end extends into (i) the column positioning slot or (ii) a volume of space directly below the column positioning slot. The disclosed methods of making column packing apparatus may include a number of additional steps in order to provide numerous apparatus components (e.g., a pneumatic pressing system, a hydraulic dampening system, etc.) and features (e.g., safety features).

The present invention is even further directed to methods of using column packing apparatus. In one exemplary method of using a column packing apparatus, the method comprises a method of packing a first column comprising positioning the first column on a column packing apparatus, wherein the step of positioning the first column causes an outer portion of the first column to be positioned relative to a pin switch end of a pin switch; and activating the column packing apparatus so as to initiate a pressure applying step, wherein the pressure applying step applies a first pressure onto internal column components of the first column based on a first location of the pin switch end. The exemplary method of packing may further comprise packing a second column, wherein the second column has an outer diameter that differs from an outer diameter of the first column, wherein the step of packing the second column comprises removing the first column adapter from the column packing apparatus; positioning the second column on the column packing apparatus, wherein the step of positioning the second column causes an outer portion of the second column to be positioned relative to the pin switch end; and activating the column packing apparatus so as to initiate a second pressure applying step, wherein the second pressure applying step applies a second pressure onto internal column components of the second column based on a second location of the pin switch end, wherein the second pressure differs from the first pressure.

These and other features and advantages of the present invention will become apparent after a review of the following detailed description of the disclosed embodiments and the appended claims.

BRIEF DESCRIPTION OF THE FIGURES

FIGS. 3A-3B depict exemplary column adapters positioned over the exemplary adapter support member of FIG. 2;

FIG. 4 depicts a column positioned on the exemplary column adapter of FIG. 3B;

DETAILED DESCRIPTION OF THE INVENTION

Figure 1:
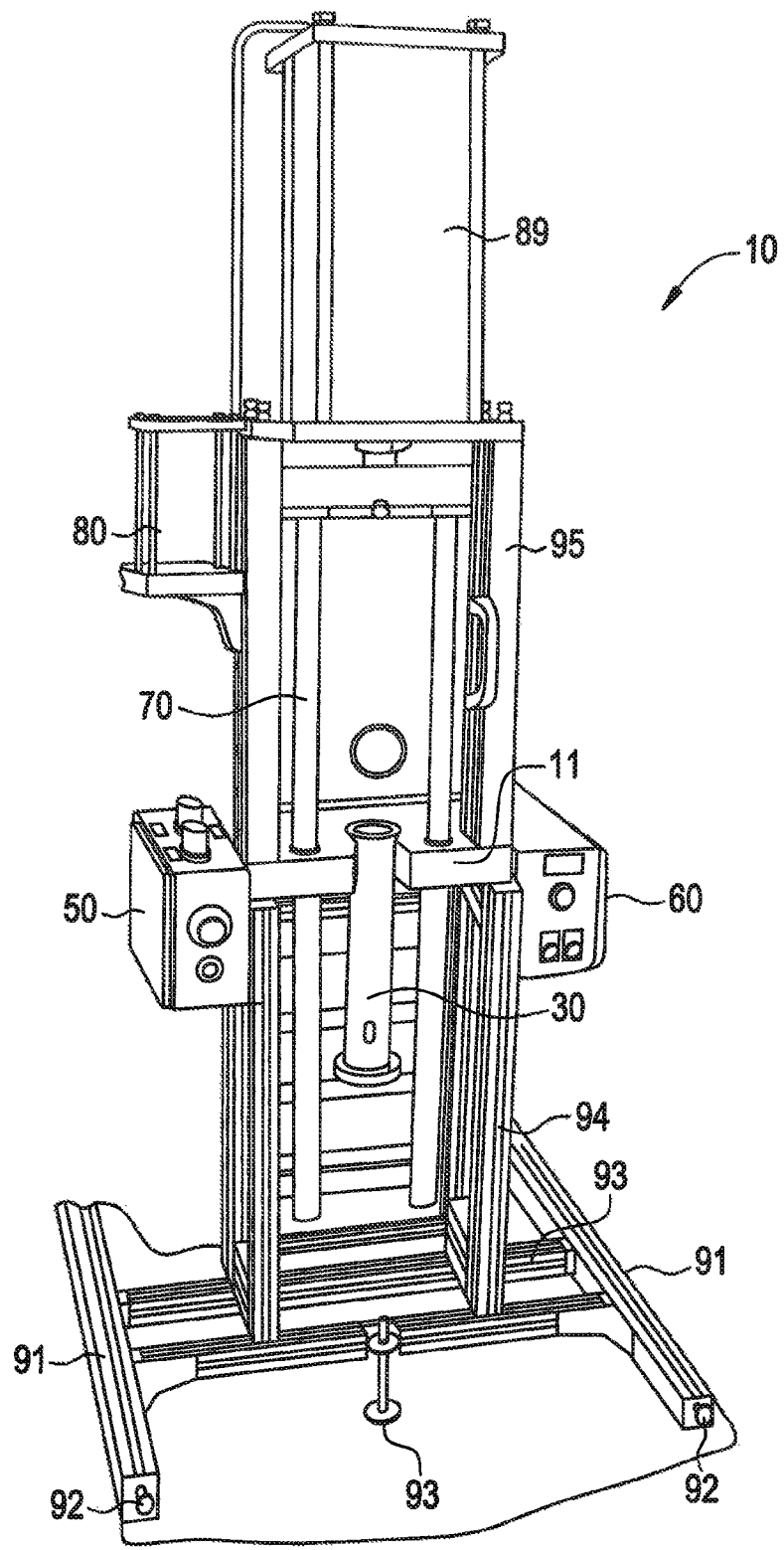
FIG. 1 depicts an exemplary column packing apparatus of the present invention.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to column packing apparatus and apparatus components suitable for use in a column packing apparatus. The present invention is further directed to methods of making a column packing apparatus, as well as methods of using a column packing apparatus to pack different sized columns.

In an exemplary embodiment, the present invention relates to a column packing apparatus for packing columns of different size comprising a column compressing member for packing media in said column, a compressing member controller for controlling pressure exerted on the media during packing, and a column holding member, wherein the column holding member includes a sensor that determines the size of the column when the column is inserted into the holding member and that communicates with the controller. The column may include a variety of chromatography columns having different shapes and sizes, which require packing with chromatography media, but an exemplary embodiment includes a cylindrical column. The media may include any chromatography media or phase materials (e.g., inorganic and/or organic) in a variety of different forms (e.g., spherical or irregular particulates), and exemplary media include metal oxide (e.g., silica) or polymeric (e.g., polyethylene) particulates. Sensors may include any optical, mechanical or electrical sensors, but an exemplary sensor may include any mechanical sensor or switch. The compressing member may include any device capable of pressing the media into the column such that the media is formed into a bed with as few void spaces or channels as possible, and an exemplary member includes a piston. The column holding member may include any device that is capable of holding and/or supporting the column during packing, but an exemplary device is the support member described herein. The compressing member controller may include any device capable of controlling the amount of pressure applied to the compressing member and an exemplary device is the pressure control station described herein.

In a further exemplary embodiment, the present invention relates to a column packing apparatus for packing columns with media comprising a column compressing member for packing the media, a compressing member controller for controlling pressure exerted on the media during packing, and a hydraulic system for generating the pressure, wherein the system includes a self degassing feature. The hydraulic system may include any system that may exert pressure, directly or indirectly, on the compressing member and an exemplary system may be the hydraulic dampening system described herein. The self degassing feature may include any device that is capable of degassing the hydraulic system, which allows for removal of undesirable gas from the hydraulic system (e.g., valves, etc.) and an exemplary device may be the degassing feature set forth herein.

One exemplary column packing apparatus of the present invention is shown in FIG. 1. As shown in FIG. 1, exemplary column packing apparatus 10 comprises an adapter support member 11 positioned so as to support a column for packing, such as exemplary column 30; a pressure control station 50; a piston activation control station 60; an oil reservoir 80 of a hydraulic dampening system; an air cylinder 89 of a pneumatic pressure-applying system; and a door 70 providing access to a packing cabinet, which contains moving parts (e.g., the pressure applying piston). All of the above-mentioned apparatus components are supported on a portable frame comprising (i) frame components 91, 94 and 95, wheels 92, and stability members 93.

As shown in FIG. 1, exemplary column packing apparatus 10 of the present invention may comprise a number of components. A description of possible apparatus components, configurations and apparatus parameters is provided below.

I. Column Packing Apparatus and Components

The column packing apparatus of the present invention comprise a number of components, which result in a column packing apparatus capable of applying a different packing pressure based on the dimensions of a column positioned on the column packing apparatus.

A. Column Packing Apparatus Components

The column packing apparatus of the present invention may include one or more of the following exemplary components. It should be noted that the column packing apparatus of the present invention may include additional components other than those specifically described below.

1. Adapter Support Member

Figure 2:
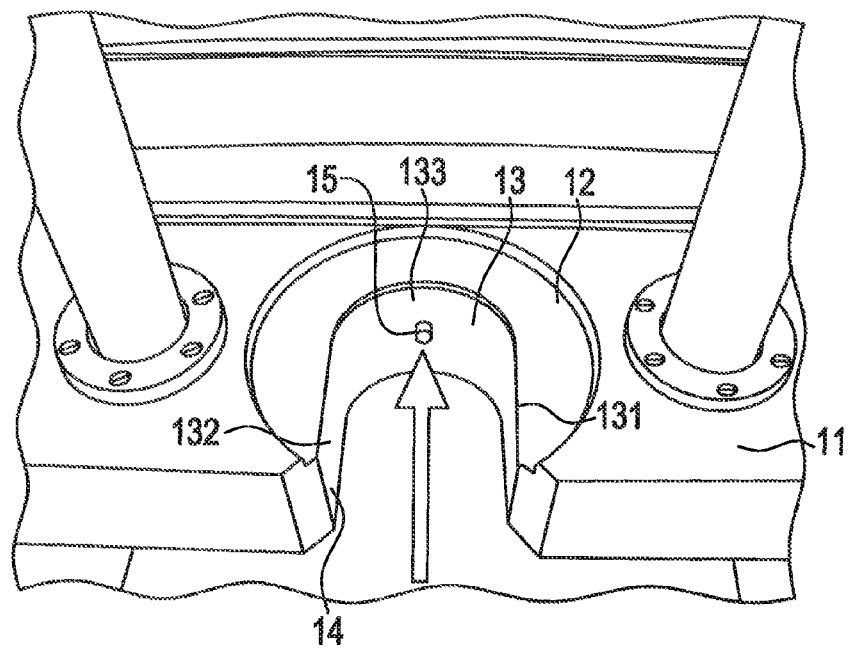
FIG. 2 depicts an exemplary adapter support member suitable for use in the exemplary column packing apparatus of FIG. 1.

The column packing apparatus of the present invention comprise at least one adapter support member such as exemplary adapter support member 11 of exemplary column packing apparatus 10 shown in FIG. 1. Referring to exemplary adapter support member 11 as shown in FIG. 2, exemplary adapter support member 11 has an upper surface 12, a lower surface (not shown), at least one sidewall 13 extending from upper surface 12 to the lower surface, and a column positioning slot 110 within adapter support member 11. Column positioning slot 110 comprises a slot mouth 14, and a portion of the at least one sidewall 13 as indicated by opposing sidewall portions 131 and 132, and curved sidewall portion 133. Slot mouth 14 has a slot mouth width (e.g., the distance between opposing sidewall portions 131 and 132) that is sized to accommodate a largest column width. In other words, slot mouth 14 has a slot mouth width that is sized so that a column having a largest column width can be inserted between opposing sidewall portions 131 and 132.

In some exemplary embodiments, the upper surface of the adapter support member has a recessed area therein. The recessed area desirably extends a depth into the upper surface of the adapter support member and surrounds at least a portion of the column positioning slot. As shown in FIG. 2, exemplary adapter support member 11 has recessed area 112. Recessed area 112 is sized so as to enhance the placement stability of a column adapter (discussed below) placed along upper surface 12 of exemplary adapter support member 11.

The adapter support member may be formed from a variety of materials including, but not limited to, metals, polymers, and fiber-reinforced composite materials (e.g., fiber-reinforced metals, thermoplastic or thermoset materials). Typically, adapter support member is formed from a metal such as stainless steel or aluminum.

The adapter support member may have dimensions that vary depending on, for example, the materials used to form the adapter support member. The adapter support member may have any dimensions (e.g., overall width, length and thickness) as long as the adapter support member is structurally able to (i) support a column for packing, and (ii) withstand the packing pressure exerted on the adapter support member. Further, as discussed above, the column positioning slot of the adapter support member (i.e., exemplary column positioning slot 110) has dimensions that enable a column for packing to be positioned within the column positioning slot.

2. Pin Switch

The column packing apparatus of the present invention further comprises at least one pin switch such as exemplary pin switch 15 shown in FIG. 2. The pin switch has a pin switch end that extends into (i) the column positioning slot (i.e., exemplary column positioning slot 110) or (ii) a volume of space directly below the column positioning slot (i.e., exemplary column positioning slot 110). As used herein, the phrase "volume of space directly below the column positioning slot" refers to a volume of space that would be outlined by the sidewalls of the column positioning slot (e.g., opposing sidewall portions 131 and 132, and curved sidewall portion 133) if the sidewalls extended below the column positioning slot (i.e., exemplary column positioning slot 110).

The pin switch is operatively adapted to adjust a packing pressure of the column packing apparatus depending on a location of the pin switch end within (i) the column positioning slot or (ii) the volume of space directly below the column positioning slot. In some embodiments, placement of a column for packing within the column packing apparatus may not alter the position of the pin switch end. In this exemplary embodiment, the column packing apparatus applies a packing pressure onto the column (and its internal contents) based on the original location (i.e., the unaltered location) of the pin switch end. Placement of a different column having larger column dimensions within the column packing apparatus may alter the position of pin switch end from an initial position to a new position. In such a case, the column packing apparatus applies a different packing pressure onto the column having larger column dimensions (and its internal contents) based on the new location (i.e., the altered location) of the pin switch end.

In other embodiments, placement of any column for packing within the column packing apparatus may alter the position of the pin switch end. For example, placement of a first column within the column packing apparatus may alter the position of pin switch end from an initial position to a first new position. In such a case, the column packing apparatus applies a packing pressure onto the first column (and its internal contents) based on the first new location (i.e., the first altered location) of the pin switch end. Placement of a different column having larger column dimensions within the column packing apparatus may alter the position of pin switch end from an initial position to a second new position, wherein the second new position is different from the first new position. In such a case, the column packing apparatus applies a different packing pressure onto the column having larger column dimensions (and its internal contents) based on the second new location (i.e., the second altered location) of the pin switch end.

In one exemplary embodiment, the pin switch is spring-loaded so as to force the pin switch end into (i) the column positioning slot or (ii) the volume of space when in an undisturbed state. In this embodiment, placement of a column for packing within the column packing apparatus either (i) does not alter the extended location of the pin switch end, or (ii) exerts a column positioning force onto the pin switch end, wherein the column positioning force opposes the force of the spring, so as to at least partially push the pin switch end toward (i) a sidewall of the column positioning slot or (ii) an imaginary sidewall of the volume of space that extends directly below the sidewall of column positioning slot.

Although the pin switch may be positioned below the adapter support member so as to extend into the volume of space directly below the column positioning slot of the adapter support member, in some desired embodiments, the pin switch extends into the column positioning slot and through the sidewall of the adapter support member as shown in FIGS. 2-3B. As shown in FIGS. 2-3B, exemplary pin switch 15 extends through curved sidewall portion 133 of column positioning slot 110 within exemplary adapter support member 11.

The above-described adapter support member and pin switch may be combined with one another to form a pressure control system suitable for use in a column packing apparatus. In one exemplary embodiment, the pressure control system comprises (1) an adapter support member having an upper surface, a lower surface, at least one sidewall extending from the upper surface to the lower surface, and a column positioning slot within the adapter support member, wherein the column positioning slot comprises a slot mouth, and a portion of the at least one sidewall, wherein the slot mouth has a slot mouth width that is sized to accommodate a largest column width; and (2) a pin switch having a pin switch end that extends into (i) the column positioning slot or (ii) a volume of space directly below the column positioning slot, wherein the pin switch is operatively adapted to adjust a packing pressure of a column packing apparatus depending on a location of the pin switch end within (i) the column positioning slot or (ii) the volume of space directly below the column positioning slot.

3. Column Adapters

Figure 3A:
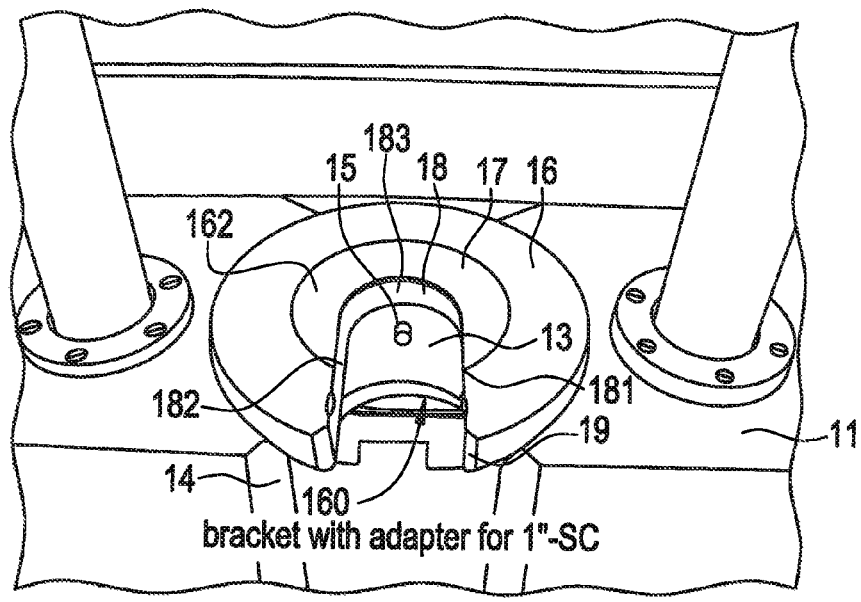

The column packing apparatus of the present invention may comprise one or more column adapters such as exemplary column adapters 16 and 26 shown in FIGS. 3A-3B. Each column adapter has similar features, but typically, different dimensions. Referring to exemplary column adapter 16 as shown in FIG. 3A, exemplary column adapter 16 has a column adapter upper surface 17, a column adapter lower surface (not shown), at least one column adapter sidewall 18 extending from column adapter upper surface 17 to the column adapter lower surface, and a column positioning slot 160 within exemplary column adapter 16. The column positioning slot 160 of exemplary column adapter 16 comprises a column adapter slot mouth 19, and a portion of the at least one column adapter sidewall 18 as indicated by opposing sidewall portions 181 and 182, and curved sidewall portion 183. Slot mouth 19 has a column adapter slot mouth width (e.g., the distance between opposing sidewall portions 181 and 182) that is sized to accommodate a width of a given column (see, for example, column 30 positioned between opposing sidewall portions 281 and 282 of column adapter 26 shown in FIG. 4).

Each column adapter is operatively adapted to position a corresponding column for packing within the column positioning slot of an adapter support member so as to cause a pin switch end to be positioned in a given location, wherein the given location is (i) an original, unaltered location or (ii) a new, altered location as discussed above.

In some exemplary embodiments, the upper surface of the column adapter has a recessed area therein. The recessed area desirably extends a depth into the upper surface of the column adapter and surrounds at least a portion of the column positioning slot of the column adapter. As shown in FIG. 3A, exemplary column adapter 16 has recessed area 162. Recessed area 162 is sized so as to enhance the placement stability of a column (see, for example, FIG. 4) placed along upper surface 17 of exemplary column adapter 16.

As with the adapter support member, the column adapter may be formed from a variety of materials including, but not limited to, metals, polymers, and fiber-reinforced composite materials (e.g., fiber-reinforced metals, thermoplastic or thermoset materials). Typically, a given column adapter is formed from a metal such as stainless steel or aluminum.

Each column adapter may have dimensions that vary depending on, for example, the materials used to form the column adapter. Each column adapter may have any dimensions (e.g., overall width, length and thickness) as long as the column adapter is structurally able to (i) support a column for packing, (ii) withstand the packing pressure exerted on the column adapter, and (iii) fit onto an upper surface of an adapter support member as discussed above. Further, as discussed above, the column positioning slot of the column adapter (i.e., exemplary column positioning slot 160) has dimensions that enable a column for packing to be positioned within the column positioning slot.

In one exemplary embodiment, the column packing apparatus of the present invention comprises a first column adapter, such as exemplary column adapter 16 shown in FIG. 3A, wherein the first column adapter has a first column adapter upper surface, a first column adapter lower surface, at least one first column adapter sidewall extending from the first column adapter upper surface to the first column adapter lower surface, and a first column positioning slot within the first column adapter, wherein the first column positioning slot comprises a first column adapter slot mouth, and at least one first column adapter sidewall, the first column adapter slot mouth having a first column adapter slot mouth width that is sized to accommodate a width of a first column, wherein the first column adapter is operatively adapted to position the first column within the column positioning slot of an adapter support member so as to cause a pin switch end to be positioned in a first location.

The above-described column packing apparatus of the present invention may further comprise a second column adapter, such as exemplary column adapter 26 shown in FIG. 3B, wherein the second column adapter has a second column adapter upper surface (e.g., upper surface 27 of exemplary column adapter 26 shown in FIG. 3B), a second column adapter lower surface, at least one second column adapter sidewall (e.g., sidewall 28 of exemplary column adapter 26 shown in FIG. 3B) extending from the second column adapter upper surface to the second column adapter lower surface, and a second column positioning slot within the second column adapter (e.g., column positioning slot 260 of exemplary column adapter 26 shown in FIG. 3B), wherein the second column positioning slot comprises a second column adapter slot mouth (e.g., column adapter slot mouth 29 of exemplary column adapter 26 shown in FIG. 3B), and at least one second column adapter sidewall (e.g., a portion of the at least one column adapter sidewall 28 as indicated by opposing sidewall portions 281 and 282, and curved sidewall portion 283), wherein the second column adapter slot mouth has a second column adapter slot mouth width that is sized to accommodate a width of a second column, wherein the second column adapter is operatively adapted to position the second column within the column positioning slot (of the adapter support member) so as to cause the pin switch end to be positioned in a second location, wherein the second location is different from the above-described first location.

In a further exemplary embodiment, the column packing apparatus of the present invention comprises a set of two or more column adapters, wherein each column adapter in the set has (i) a column adapter upper surface, (ii) a column adapter lower surface, (iii) at least one column adapter sidewall extending from the column adapter upper surface to the column adapter lower surface, and (iv) an adapter column positioning slot within each column adapter, wherein the adapter column positioning slot comprises (a) a column adapter slot mouth, and (b) at least one column adapter sidewall, wherein the column adapter slot mouth has a column adapter slot mouth width that is sized to accommodate a width of a spring column. In this exemplary embodiment, the set of two or more column adapters is operatively adapted to position two or more spring columns within the column positioning slot of a given adapter support member so as to cause a pin switch end to be positioned in two or more different locations.

4. Columns

The column packing apparatus of the present invention may further comprise one or more columns such as exemplary column 30 shown in FIGS. 1 and 4. Typically, conventionally sized columns, such as columns having a 25 mm (1 inch) inner diameter (ID) and columns having a 50 mm (2 inches) ID, may be used in combination with the column packing apparatus of the present invention. In some embodiments, the column packing apparatus of the present invention and components used therein may have specific dimensions (e.g., a slot mouth width) that match (i) conventionally sized columns such as those described above, or (ii) specialty columns that can only be used with the column packing apparatus of the present invention and components used therein.

As discussed above, the components of the column packing apparatus of the present invention may be sized to accommodate columns of various sizes. Desirably, the column packing apparatus of the present invention and components used therein enable two (or three or four or more) different sized columns to be packed on the same column packing apparatus.

As shown in FIG. 4, exemplary column 30 is positioned on column adapter 26 so that a lower surface 32 of a flange portion 31 of exemplary column 30 contacts upper surface 27 of column adapter 26. Exemplary column 30 extends through column positioning slot 110 of adapter support member 11 and adapter column positioning slot 260 of column adapter 26. Although not shown in FIG. 4, placement of exemplary column 30 in column adapter 26 results in an outer portion of exemplary column 30, namely, an outer sidewall portion of exemplary column 30 below flange portion 31, exerts a column-positioning force on pin switch 15, which signals exemplary column packing apparatus 10 to apply a specific packing pressure onto exemplary column 30 and its internal components (not shown).

5. Packing Adapters

Figure 5:
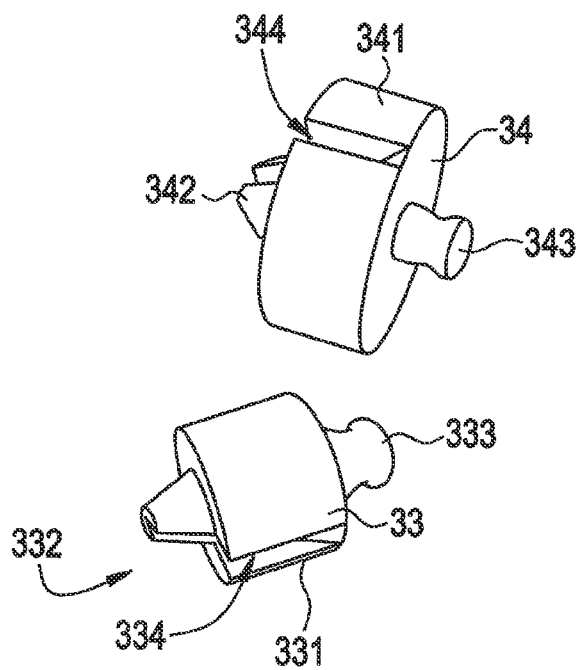
FIG. 5 depicts exemplary packing adapters suitable for use in the exemplary column packing apparatus of FIG. 1.

The column packing apparatus of the present invention may further comprise one or more packing adapters such as exemplary packing adapters 33 and 34 shown in FIG. 5. Each packing adapter has similar features, but typically, different dimensions. Referring to exemplary packing adapter 33 shown in FIG. 5, exemplary packing adapter 33 comprise a central body portion 331 having a outer diameter substantially similar to an inner diameter of a corresponding column; a tapered end 332 that assists in the engagement of internal column components (not shown) to be inserted into the corresponding column; a male connector 333 on an opposite end from tapered end 332, wherein male connector 333 is designed to engage with a female connector within a sliding member as discussed below; and a slot 334 within central body portion 331, wherein slot 334 assists in guidance of a capillary (see, for example, capillary 44 in FIGS. 8B-8D) within the internal column components (not shown).

Like exemplary packing adapter 33, exemplary packing adapter 34 comprise a central body portion 341 having a outer diameter substantially similar to an inner diameter of a corresponding column, and larger than that of exemplary packing adapter 33; a tapered end 342 that assists in the engagement of internal column components (not shown) to be inserted into the corresponding column; a male connector 343 on an opposite end from tapered end 332; and a slot 344 within central body portion 341.

Each packing adapter is operatively adapted to align internal column components with a column positioned within the column positioning slot of an adapter support member as discussed further below. The packing adapter enables hands-free packing of a given column as described below.

As with the adapter support member, the packing adapter may be formed from a variety of materials including, but not limited to, metals, polymers, and fiber-reinforced composite materials (e.g., fiber-reinforced metals, thermoplastic or thermoset materials). Typically, a given packing adapter is formed from a metal such as stainless steel or aluminum.

Each packing adapter may have dimensions that vary depending on, for example, a given column size, and dimensions of the other components used in the column packing apparatus. Typically, each packing adapter has a central body portion having a circular cross-sectional configuration, and an outer diameter that is substantially similar to an inner diameter of a corresponding column. In one exemplary embodiment, a set of packing adapters may be used in combination with the column packing apparatus of the present invention, wherein the set contains at least one packing adapter corresponding to each column capable of being packed with the column packing apparatus.

6. Hydraulic Dampening System

The column packing apparatus of the present invention may further comprise a hydraulic dampening system. Components of a given hydraulic dampening system may include, but are not limited to, cylindrical rods such as exemplary cylindrical rods 37 and 38 shown in FIGS. 8A-8D; corresponding air cylinders such as exemplary air cylinders 87 and 88 (shown in FIG. 8D) dimensioned to receive cylindrical rods 37 and 38 respectively; an oil reservoir such as exemplary oil reservoir 80 shown in FIG. 12; and oil such as exemplary oil 81 shown in FIG. 12.

Figure 8A:
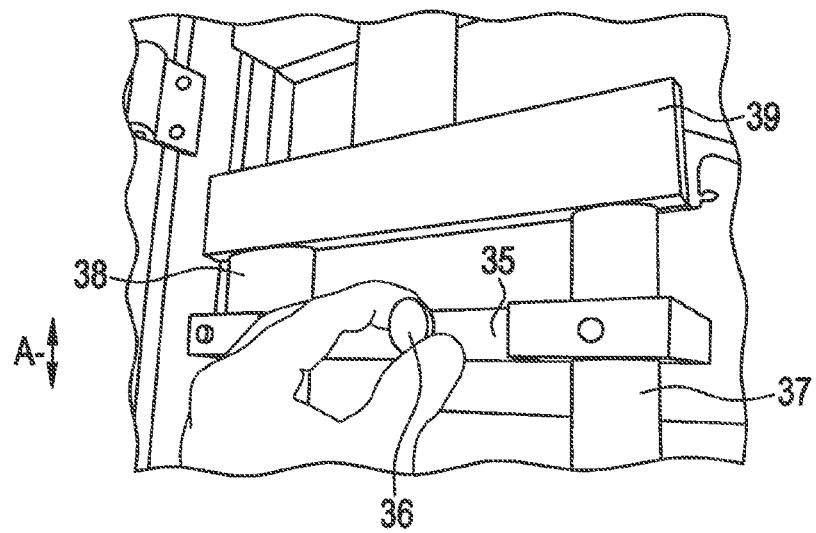
FIGS. 8A-8D depict various stages of an exemplary packing process utilizing the exemplary sliding crossbar/packing adapter assembly shown in FIG. 7A and the exemplary column adapter of FIG. 3A.
Figure 8B:
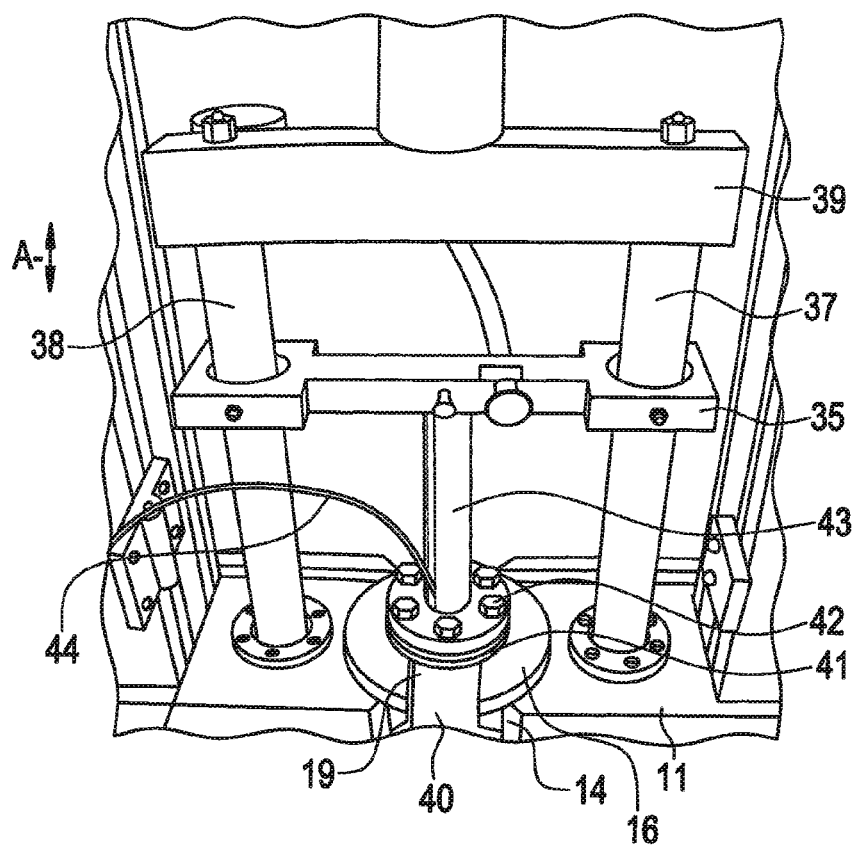
Figure 8C:
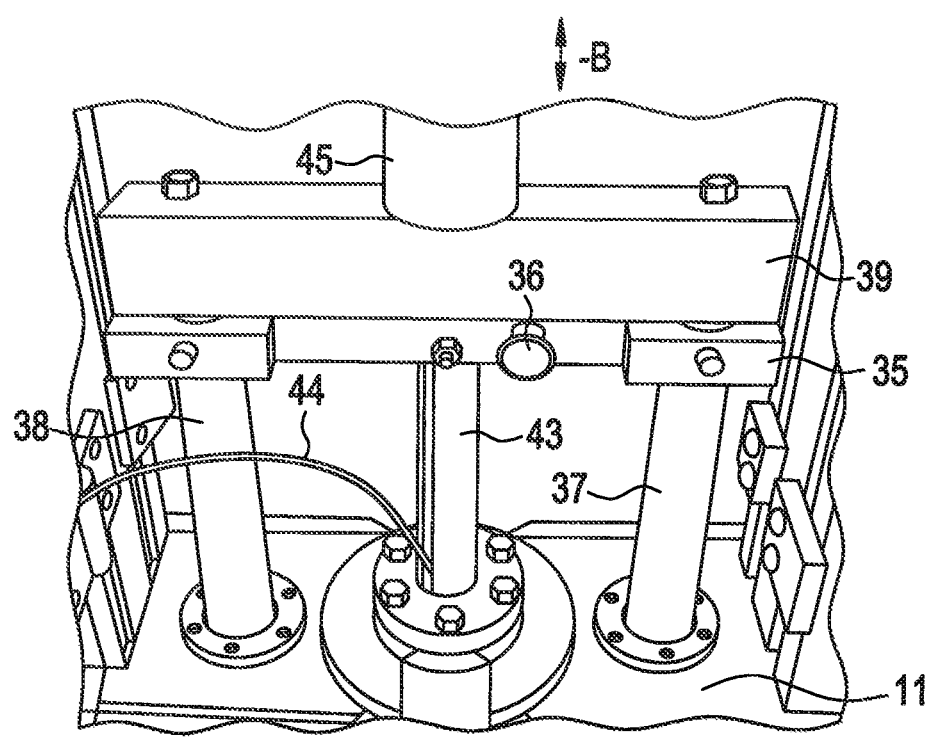
Figure 8D:
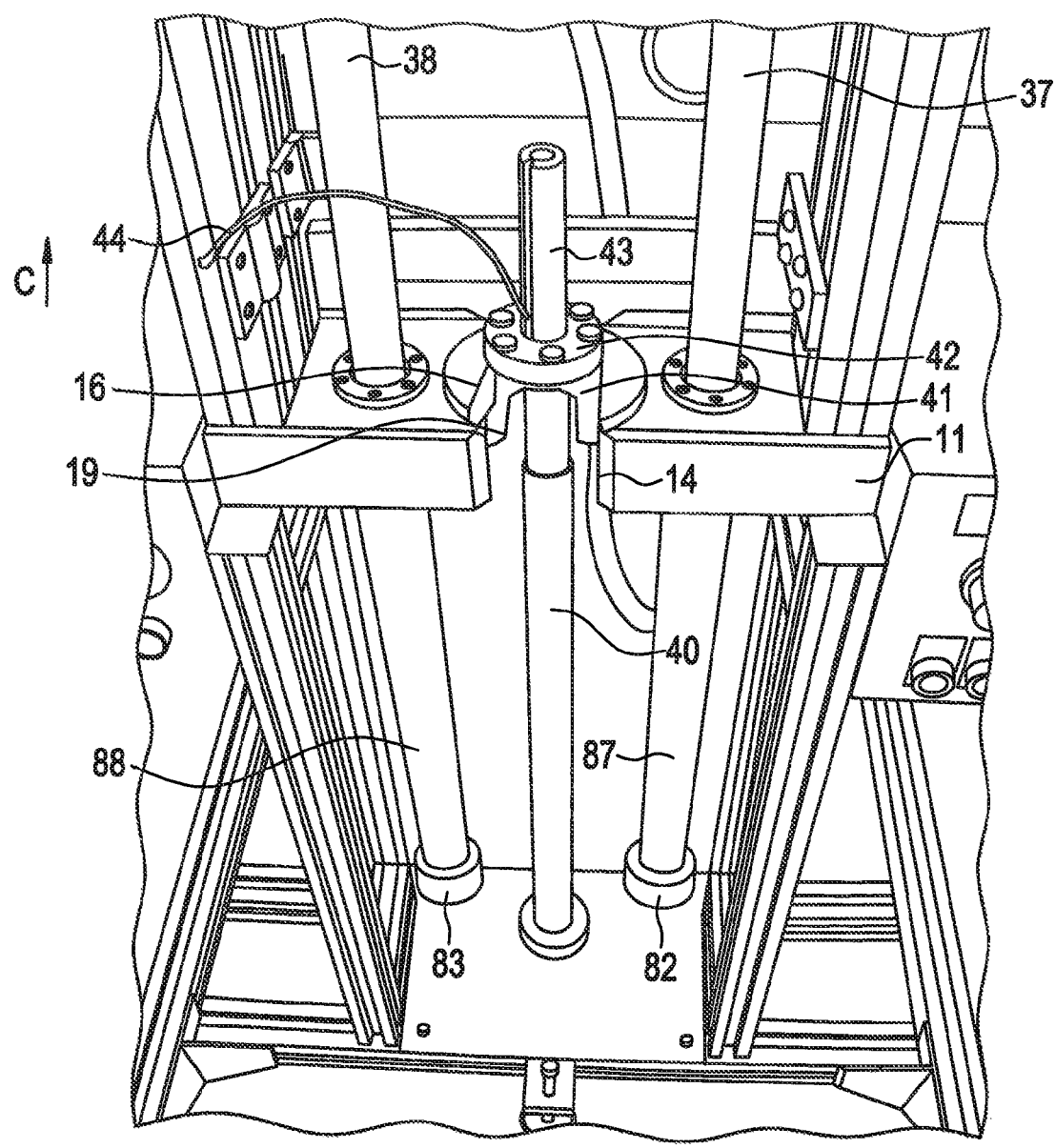

As shown in FIGS. 8B-8D, exemplary cylindrical rods 37 and 38 are typically positioned on opposite sides of the adapter support member and its column positioning slot (e.g., adapter support member 11 and column positioning slot positioning slot 110). As shown in FIG. 8D, exemplary air cylinders 87 and 88 comprise easily accessible air bleed valves 82 and 83 respectively, which may be used as needed to quickly release air pressure within exemplary air cylinders 87 and 88.

Figure 12:
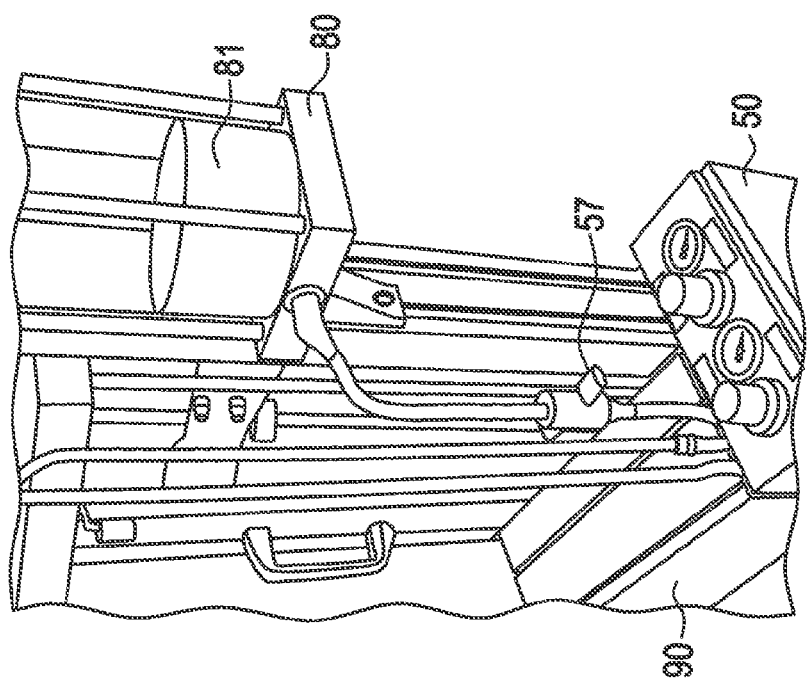
FIG. 12 depicts an exemplary hydraulic system suitable for use in the exemplary column packing apparatus of FIG. 1.

As shown in FIG. 12, in one exemplary embodiment of the present invention, the column packing apparatus comprises a hydraulic dampening system comprising an oil reservoir and tubing that connects the oil reservoir with other components of the hydraulic dampening system, wherein the oil reservoir is located at a highest point of the hydraulic dampening system. Such a configuration enables the hydraulic dampening system to be a self-degassing or self-venting system. Although not shown in FIG. 12, the hydraulic dampening system also comprises a built-in filter for filtering the oil.

Referring to FIG. 12, exemplary column packing apparatus 10 comprises oil reservoir 80 containing oil 81, wherein oil reservoir 80 is positioned at a highest point within the hydraulic dampening system of exemplary column packing apparatus 10.

7. Pneumatic Pressure-Applying System

The column packing apparatus of the present invention may further comprise a pneumatic pressure-applying system. Components of the pneumatic pressure-applying system may include, but are not limited to, a crossbar member such as exemplary crossbar member 39 shown in FIGS. 8A-8D; a piston such as exemplary piston 45 shown in FIGS. 8A-8C; and an air cylinder such as exemplary air cylinder 89 shown in FIG. 1.

8. Sliding Member

The column packing apparatus of the present invention may further comprise a sliding member such as exemplary sliding member 35 shown in FIGS. 6-8C. Referring to exemplary sliding member 35 shown in FIGS. 6-8C, exemplary sliding member 35 is operatively adapted to engage with and disengage with crossbar member 39 so as to move freely along cylindrical rods 37 and 38 of the hydraulic dampening system. Exemplary sliding member 35 disengages with crossbar member 39 by pulling out knob 36 located on sliding member 35. Exemplary sliding member 35 engages with crossbar member 39 by positioning sliding member 35 adjacent crossbar member 39 and pushing in knob 36.

Figure 6:
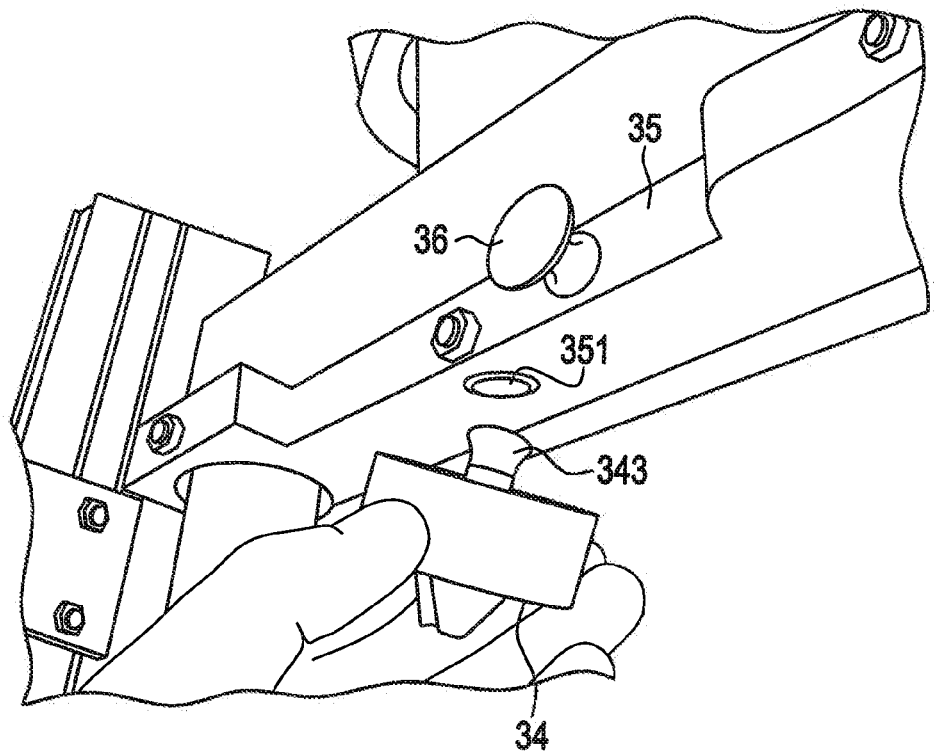
FIG. 6 depicts an exemplary packing adapter of FIG. 5 being connected to an exemplary sliding crossbar suitable for use in the exemplary column packing apparatus of FIG. 1.

As discussed above and as shown in FIG. 6, a packing adapter may be connected to the sliding member. As shown in FIG. 6, exemplary packing adapter 34 may be connected to sliding member 35 via male connector 343 of exemplary packing adapter 34 and a corresponding female connector 351 located along an outer surface of sliding member 35. Although shown as male and female connectors, it should be noted that a given packing adapter may be connected to the sliding member via any possible connection method. Desirably, a given packing adapter may be connected to a sliding member via a tool-free, quick-fit male/female connection method, wherein simply inserting a male connector of a given packing adapter into a corresponding female connector of a sliding member locks the packing adapter in place until an opposite force is used to remove the packing adapter from the sliding member.

Figure 7A:
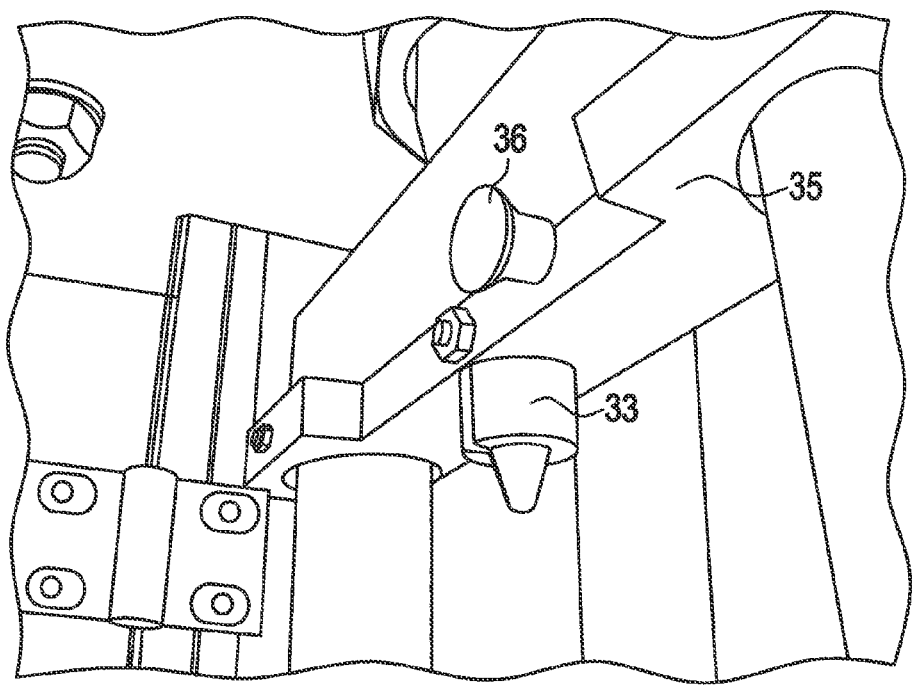
FIGS. 7A-7B depict exemplary packing adapters connected to an exemplary sliding crossbar suitable for use in the exemplary column packing apparatus of FIG. 1.
Figure 7B:
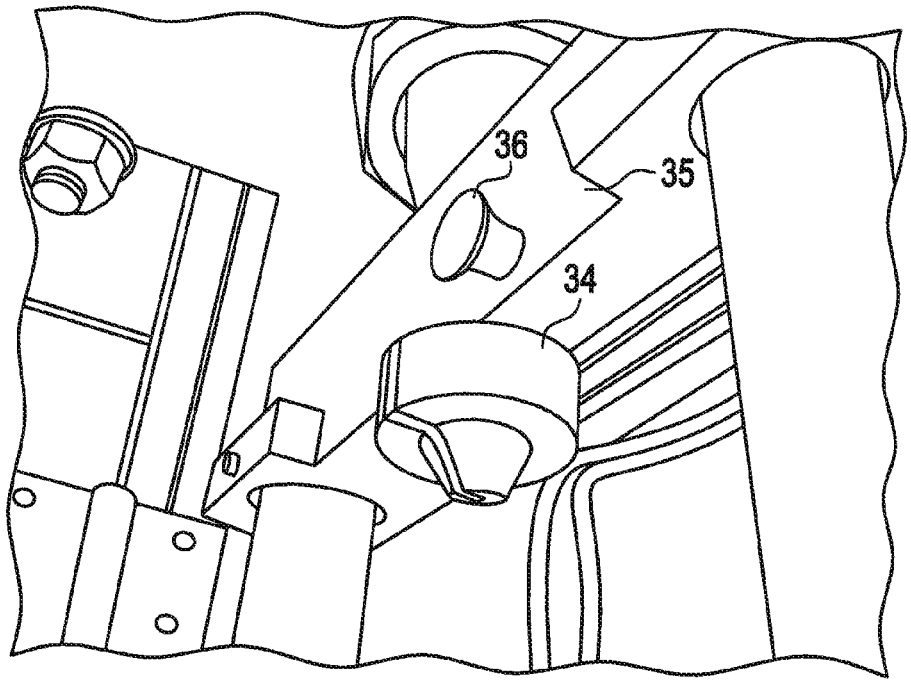

As shown in FIG. 7A, exemplary packing adapter 33 may be connected to sliding member 35 via male connector 333 of exemplary packing adapter 33 and corresponding female connector 351 (not shown) located along an outer surface of sliding member 35. Likewise, as shown in FIG. 7B, exemplary packing adapter 34 may be connected to the same sliding member, namely, sliding member 35, via male connector 343 of exemplary packing adapter 34 and corresponding female connector 351 (not shown) of sliding member 35.

Once connected to sliding member 35, packing adapter 33, for example, may be used to assist in the alignment of internal column components with a corresponding column (to be packed) as shown in FIGS. 8A-8D. As shown in FIG. 8A, exemplary sliding member 35 with packing adapter 33, when disengaged from crossbar 39, moves freely along cylindrical rods 37 and 38 of the hydraulic dampening system in either an "up" or "down" direction as indicated by arrow A.

As shown in FIG. 8B, exemplary sliding member 35 with packing adapter 33 is moved downward toward a column 40 (to be packed) positioned on column adapter 16 along adapter support member 11. Internal column components 43 may be positioned between sliding member 35 and an upper flange 42 connected to flange portion 41 of column 40. Exemplary packing adapter 33, attached to sliding member 35, assists in the alignment and positioning of internal column components 43 between sliding member 35 and column 40. As shown in FIG. 8B, once aligned, internal column components 43 may be held in place by sliding member 35 (with packing adapter 33 attached thereto) and column 40 without the need of an operator holding internal column components 43 in place by hand.

As shown in FIG. 8C, once the pressing step is initiated, piston 45 and crossbar 39 move downward as shown by arrow B and contact sliding member 35, reconnecting sliding member 35 with crossbar 39. Piston 45, crossbar 39 and sliding member 35 (with packing adapter 33 attached thereto) apply a pre-assigned packing pressure onto internal column components 43 without the need of an operator holding internal column components 43 in place by hand.

As shown in FIG. 8D, once a desired amount of packing has taken place, piston 45 and crossbar 39 move upward as shown by arrow C and out of the way so that packed column 40 can be removed from column adapter 16 and adapter support member 11 thru (i) adapter column positioning slot mouth 19 of column adapter 16 and (ii) column positioning slot mouth 14 of adapter support member 11.

It should be noted that the above-described sliding member can be used on any column packing apparatus to provide hands-free packing of a given column. In one exemplary embodiment of the present invention, the present invention is directed to a column packing apparatus comprising a sliding member operatively adapted to engage with and disengage with a crossbar member so as to move freely along rods of a hydraulic dampening system, wherein the rods are positioned on opposite sides of a column positioning member, and wherein the sliding member has a connector capable of engaging with a packing adapter that is operatively adapted to align internal column components (for packing into a column) with a column positioned along the column positioning member.

9. Pressure Control Station

Figure 9:
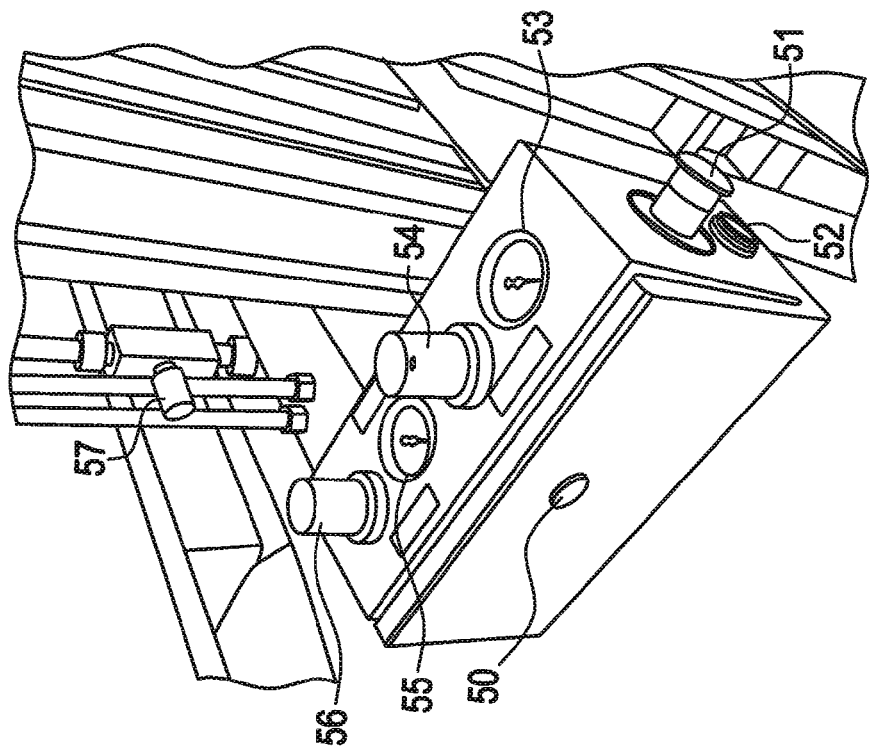
FIG. 9 depicts an exemplary pressure control station suitable for use in the exemplary column packing apparatus of FIG. 1.

The column packing apparatus of the present invention may further comprise a pressure control station such as exemplary pressure control station 50 shown in FIGS. 1 and 9. As shown in FIG. 9, exemplary pressure control station 50 may comprise multiple pressure indication gauges such as pressure indication gauges 53 and 55, multiple pressure setting knobs, one for each pressure indication gauge, such as pressure setting knobs 54 and 56, packing speed controller 57, emergency stop button 51, and system activation button 52.

Each of exemplary pressure setting knobs 54 and 56 may be used by an operator to adjust a pressure setting to a desired pressure within a given pressure range. For example, pressure setting knob 54 may be used by an operator to adjust a pressure setting to a desired pressure within a relatively low pressure range as indicated on pressure indication gauge 53. The selected low pressure setting may be suitable for use with a given column, such as a 25 mm ID column (e.g., such as exemplary column 40 shown in FIG. 8D). In such a case, when the 25 mm ID column (e.g., exemplary column 40 shown in FIG. 8D) is placed within the column packing apparatus of the present invention, the 25 mm ID column either (i) does not alter an original position of a pin switch end or (ii) alters the position of the pin switch end to a first location; however, in either situation, the location of the pin switch end signals to the column packing apparatus to apply an amount of pressure as set by the operator within the relatively low pressure range indicated on pressure indication gauge 53.

Similarly, pressure setting knob 56 may be used by an operator to adjust a pressure setting to a desired pressure within a relatively high pressure range as indicated on pressure indication gauge 55. The selected high pressure setting may be suitable for use with, for example, a 50 mm ID column (e.g., exemplary column 30 shown in FIG. 4). When the 50 mm ID column (e.g., exemplary column 30 shown in FIG. 4) is placed within the column packing apparatus of the present invention, the 50 mm ID column alters the position of the pin switch end to a second location. The location of the pin switch end in the second location signals to the column packing apparatus to apply an amount of pressure as set by the operator within the relatively high pressure range indicated on pressure indication gauge 55.

Although only two pressure setting knobs and two corresponding pressure indication gauges are shown in FIG. 9, it should be noted that the column packing apparatus of the present invention may include more than two pressure setting knobs and more than two corresponding pressure indication gauges so that three or more different pressure ranges are utilized by the column packing apparatus in response to three or more locations of a given pin switch end.

Packing speed controller 57 may be used by an operator to adjust the speed of exemplary piston 45 and crossbar 39 as exemplary piston 45 and crossbar 39 move downward during a column packing step. Emergency stop button 51 can be pushed by an operator to immediately depressurization of the column packing apparatus (i.e., to immediately stop downward movement of exemplary piston 45 and crossbar 39). Further, system activation button 52 can be pushed by an operator to activate the column packing apparatus.

10. Piston Activation Control Station

Figure 10:
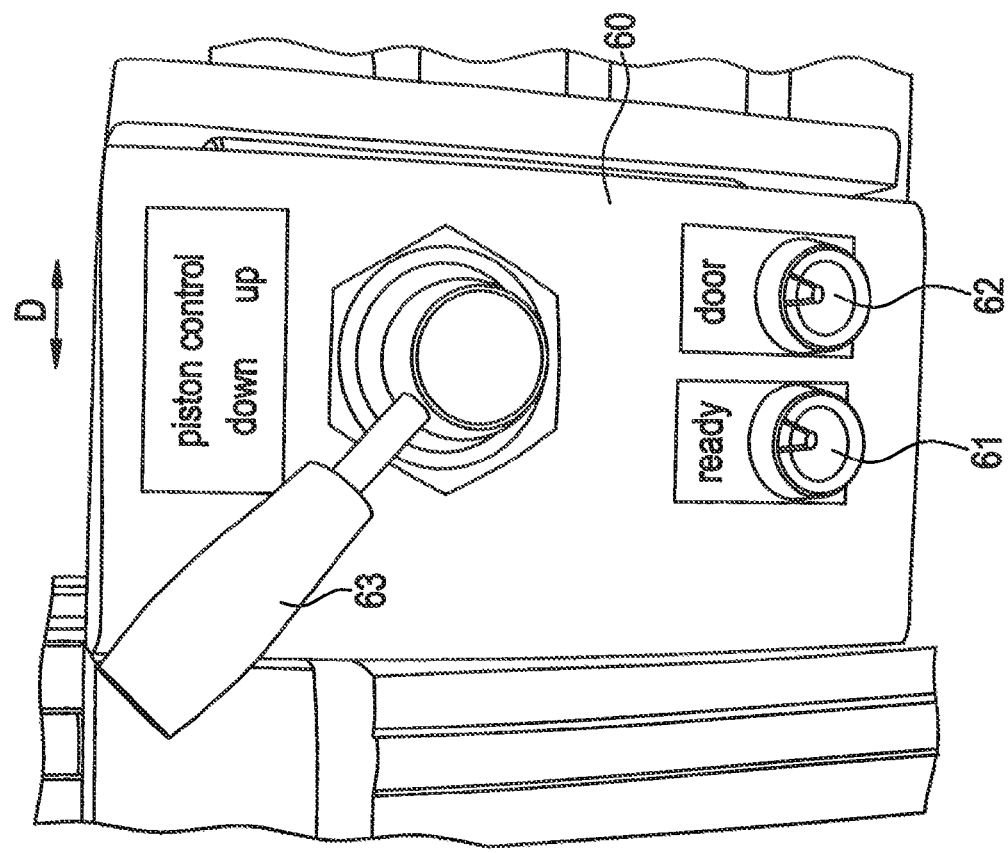
FIG. 10 depicts an exemplary piston activation control station suitable for use in the exemplary column packing apparatus of FIG. 1.

The column packing apparatus of the present invention may comprise a piston activation control station such as exemplary piston activation control station 60 shown in FIGS. 1 and 10. As shown in FIG. 10, exemplary piston activation control station 60 may comprise system status indicator buttons including, but not limited to, (1) a system ready button such as exemplary system ready button 61, and (2) a door safety button such as exemplary door safety button 62. Exemplary piston activation control station 60 may further comprise a piston up/down control such as exemplary piston up/down control 63.

Exemplary system ready button 61 may be used to indicate to an operator that the system is pressurized and ready for a column packing step. For example, when system ready button 61 is "on" (i.e., lit), the "on" status may indicate to the operator that the system is pressurized and ready for a column packing step. The operator may then initiate downward movement of piston 45 and crossbar 39 by moving exemplary piston up/down control 63 to a "down" position (i.e., to the left as indicated by arrow D).

Exemplary door safety button 62 may be used to indicate to an operator that it is safe to open door 70 (shown in FIG. 11) without danger after piston 45 and crossbar 39 have stopped moving downward. For example, when door safety button 62 is "on" (i.e., lit), the "on" status may indicate to the operator that piston 45 and crossbar 39 have stopped moving downward, and it is safe to open door 70. The operator may then initiate upward movement of piston 45 and crossbar 39 by moving exemplary piston up/down control 63 to an "up" position (i.e., to the right as indicated by arrow D).

11. Safety Door(s)

Figure 11:
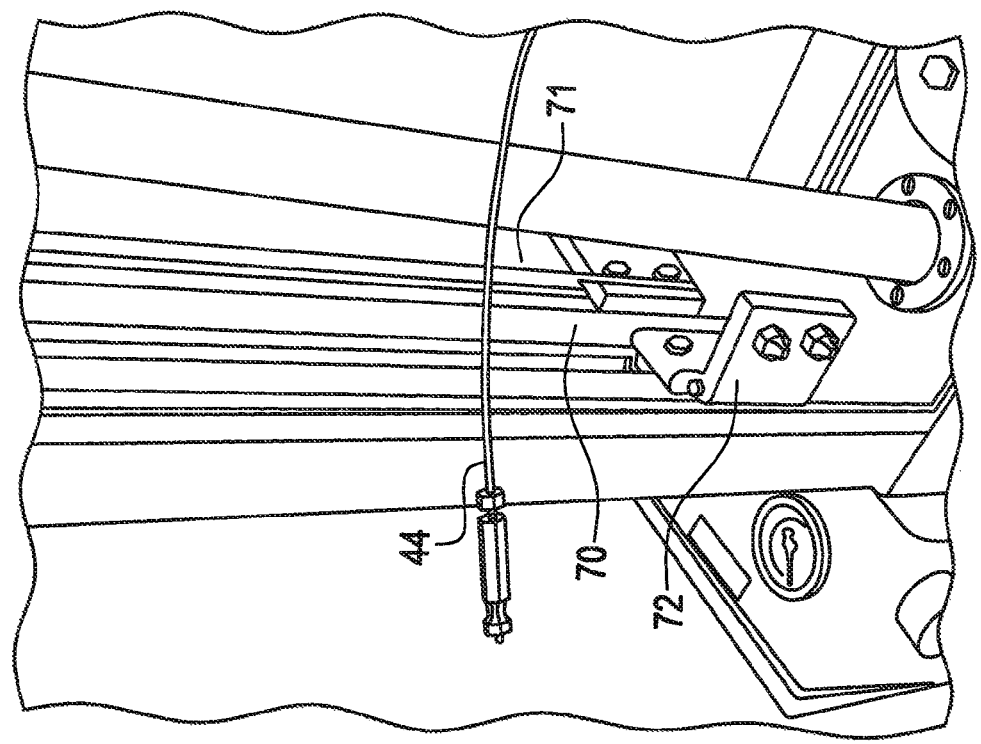
FIG. 11 depicts an exemplary door for use in the exemplary column packing apparatus of FIG. 1.

The column packing apparatus of the present invention may further comprise one or more safety doors such as exemplary safety door 70 shown in FIGS. 1 and 11. As shown in FIG. 11, exemplary safety door 70 may be attached to apparatus framing 95 via one or more hinges 72. Desirably, hinges 72 enable each safety door 70 to open at least 90 degrees from an initial, "closed" position. When the column packing apparatus comprise safety doors on opposite sides of the packing chamber, desirably each door opens at least 90 degrees from an initial, "closed" position and swings open to the same side of the apparatus (i.e., so that the doors are substantially aligned with one another when in a fully opened position).

As shown in FIG. 11, exemplary safety door 70 may also comprise a slot 71 extending along a length of safety door 70. Slot 71 enables an operator to guide capillary 44 from outside safety door 70 and the packing chamber.

Each safety door may be formed from a variety of materials including, but not limited to, glass or polycarbonate. Desirably, each safety door is formed from polycarbonate.

12. Other Column Packing Apparatus Components

The column packing apparatus of the present invention may further comprise a number of additional components such as safety enhancing components. Additional components include, but are not limited to, a magnetic door interlock system such as exemplary magnetic door interlock system 74 shown in FIG. 13; a door release sensor such as exemplary door release sensor 75 shown in FIG. 14; and a pneumatic door sensor such as exemplary pneumatic door sensor 76 shown in FIG. 15.

Figure 13:
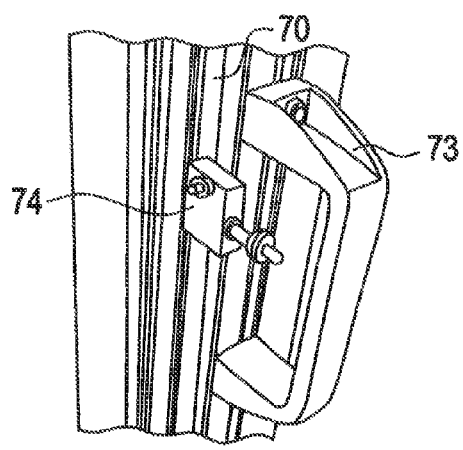
FIG. 13 depicts an exemplary magnetic door interlock system suitable for use in the exemplary column packing apparatus of FIG. 1.

Exemplary magnetic door interlock system 74 shown in FIG. 13 may be used to magnetically engage safety door 70 to a portion of apparatus framing member 95 (see FIG. 1) in the vicinity, for example, of door handle 73.

Figure 14:
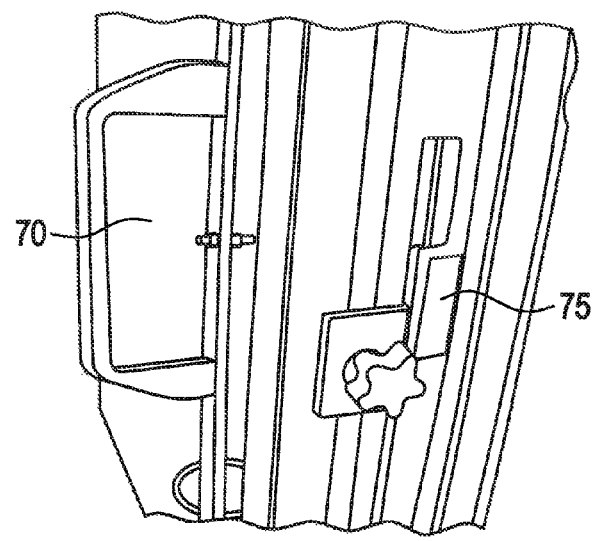
FIG. 14 depicts an exemplary door release sensor suitable for use in the exemplary column packing apparatus of FIG. 1.

Exemplary door release sensor 75 shown in FIG. 14 may be used to open safety door 70 without depressurizing the pneumatic pressure-applying system. For example, when exemplary door release sensor 75 is aligned with a packing adapter connected to a sliding member (not shown) indicating that the packing adapter, the sliding member, the internal column contents, and the column to be packed are in a substantially stable position, exemplary door release sensor 75 may allow safety door 70 to be opened without depressurizing the pneumatic pressure-applying system.

Figure 15:
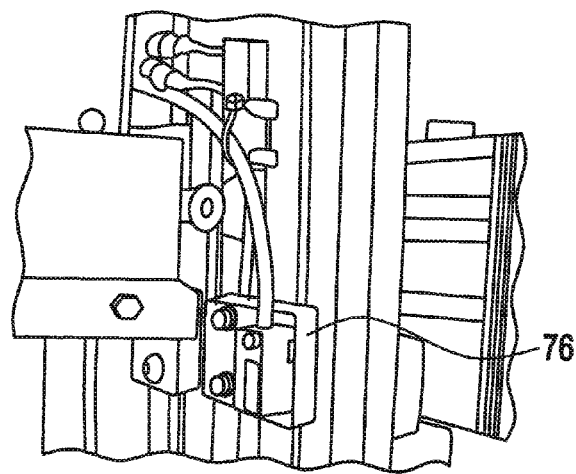
FIG. 15 depicts an exemplary pneumatic door sensor suitable for use in the exemplary column packing apparatus of FIG. 1.

Exemplary pneumatic door sensor 76 shown in FIG. 15 may be used to automatically depressurize the pneumatic pressure-applying system when any safety door 70 is opened.

II. Methods of Making Column Packing Apparatus

The present invention is also directed to methods of making column packing apparatus. In one exemplary method, the method of making a column packing apparatus comprises providing an adapter support member having an upper surface, a lower surface, at least one sidewall extending from the upper surface to the lower surface, and a column positioning slot within the adapter support member, wherein the column positioning slot comprises a slot mouth, and a portion of the at least one sidewall, the slot mouth having a slot mouth width that is sized to accommodate a largest column width; providing a pin switch having a pin switch end, wherein the pin switch is operatively adapted to adjust a packing pressure of the column packing apparatus depending on a location of the pin switch end; and positioning the pin switch so that the pin switch end extends into (i) the column positioning slot or (ii) a volume of space directly below the column positioning slot.

Methods of making a column packing apparatus of the present invention may further comprise providing a set of two or more column adapters, wherein each column adapter in the set has a column adapter upper surface, a column adapter lower surface, at least one column adapter sidewall extending from the column adapter upper surface to the column adapter lower surface, and an adapter column positioning slot within each column adapter, the adapter column positioning slot comprising a column adapter slot mouth, and at least one column adapter sidewall, the column adapter slot mouth having a column adapter slot mouth width that is sized to accommodate a width of a spring column, wherein (i) each column adapter is sized to rest along the upper surface of the adapter support member so that the adapter column positioning slot of the column adapter aligns with the column positioning slot of the adapter support member, and (ii) the set of column adapters is operatively adapted to position two or more spring columns within the column positioning slot so as to cause the pin switch end to be positioned in two or more different locations.

Methods of making a column packing apparatus of the present invention may even further comprise providing a sliding member operatively adapted to engage with and disengage with a crossbar member so as to move freely along rods of a hydraulic dampening system, the rods being positioned on opposite sides of the column positioning member, the sliding member having a connector capable of engaging with a packing adapter, the packing adapter being operatively adapted to align internal column components with a column positioned along the column positioning member.

The exemplary methods of making a column packing apparatus may even further comprise providing a hydraulic dampening system comprising an oil reservoir and tubing that connects the oil reservoir with other components of the hydraulic dampening system; and positioning the oil reservoir at a location comprising a highest point of the hydraulic dampening system.

The above-described exemplary method of making a column packing apparatus may include any number of additional steps. Suitable additional steps may include, but are not limited to, incorporating any of the above-described apparatus components either alone or in combination with one another into a column packing apparatus; providing at least 2 (or 3, or 4, or 5, or 6, or 7, or 8, etc,) column adapters for the column packing apparatus, wherein each column adapter changes a location of a given column relative to a pin switch end of a pin switch; and providing at least 2 (or 3, or 4, or 5, or 6, or 7, or 8, etc,) packing adapters for the column packing apparatus, wherein each packing adapter has an outer diameter that corresponds to an inner diameter of a corresponding column for packing.

The method of making a column packing apparatus desirably results in a column packing apparatus having one or more of the following properties:

a) a column packing apparatus capable of accommodating at least two different sized columns (e.g., a 25 mm ID column and a 50 mm ID column);

b) the ability to apply a constant pressure of about 2000 psi for any column being packed;

c) the ability to adjust the packing pressure for any given pressure range (e.g., the low and high pressure ranges discussed above) from as low as 0 psi up to about 2000 psi;

d) a display of the packing pressure used;

e) the ability to automatically change a maximum allowable pressure delivered to a column based on the dimensions of the column being packed;

f) a universal adapter support member (e.g., exemplary adapter support member 11);

g) the ability to easily exchange column adapters (e.g., exemplary column adapters 16 and 26) and packing adapters (e.g., exemplary packing adapters 33 and 34) when switching from one sized column to be packed to a different sized column to be packed;

h) the ability to adjust a packing speed from zero to a system maximum speed;

i) smooth movement of the piston (e.g., exemplary piston 45) during packing (i.e., piston movement without any pressure peaks at constant packing speed);

j) automatic detection of column dimension of a column to be packed when placed into the system for packing, and automatic adjustment of the packing pressure accordingly;

k) a hands-free packing step as discussed above;

l) safety features that prevent an operator from reaching into the packing chamber during an active phase of packing (i.e., system piston moving);

m) the ability to maintain a constant force even after springs within a column have been compressed and the packing bed is settled and in equilibrium with the applied pressure;

n) fasteners/bolts to secure a column inlet while force is being applied to the column;

o) a sealed, leaked-free and maintenance-free, oil-containing hydraulic system;

p) a system that does not allow air to enter and/or accumulate in the hydraulic dampening system;

q) if air should accumulate in the hydraulic dampening system, the ability to easily bleed air out of the system without any disassembling of the equipment;

r) an emergency shut-off switch that completely depressurizes the apparatus when activated;

s) a minimum operating pressure of about 5 bar;

t) an apparatus design that complies with all country regulations (e.g., EU-regulations) applicable to such an apparatus;

u) alternative versions such as a 'stand-alone' large version and an "extra-small" version that could be installed, for example, within a fume hood;

v) apparatus dimensions for the "stand-alone" large version to be as small as possible;

w) an optimized apparatus height so as to minimum size and space requirements;

x) safety doors that prevent the operator from reaching into the packing chamber during operation (i.e., moving piston) and trigger a safety circuit that depressurizes the apparatus when the safety door is opened during the active packing operation; and y) full and easy access to the column head after the active packing operation (i.e., when no parts are moving), but while the column is still being kept under pressure.

III. Methods of Using Column Packing Apparatus

The present invention is further directed to methods of using column packing apparatus. In one exemplary embodiment of the present invention, the method of using a column packing apparatus comprises a method of packing a first column comprising positioning the first column on a column packing apparatus, wherein the step of positioning the first column causes an outer portion of the first column to be positioned relative to a pin switch end of a pin switch; and activating the column packing apparatus so as to initiate a pressure applying step, wherein the pressure applying step applies a first pressure onto internal column components of the first column based on a first location of the pin switch end.

The exemplary method of packing a column may further comprise packing a second column, wherein the second column has an outer diameter that differs from an outer diameter of the first column, wherein the step of packing the second column comprises removing the first column adapter from the column packing apparatus; positioning the second column on the column packing apparatus, wherein the step of positioning the second column causes an outer portion of the second column to be positioned relative to the pin switch end; and activating the column packing apparatus so as to initiate a second pressure applying step, wherein the second pressure applying step applies a second pressure onto internal column components of the second column based on a second location of the pin switch end, wherein the second pressure differs from the first pressure.

The exemplary method of packing a column may even further comprise manually setting the first and second pressures prior to the positioning step so that the column packing apparatus applies a predetermined amount of pressure based on the first and second locations of the pin switch end. For example, an operator may adjust pressure setting gauges 52 and 54 so as to provide a first pressure for a 25 mm ID column, and a second pressure for a 50 mm ID column when either the 25 mm ID column or the 50 mm ID column is positioned relative to a given pin switch end.

In one desired embodiment, the method of packing a first column comprises positioning a first column over an upper surface of an adapter support member (e.g., upper surface 12 of exemplary adapter support member 11) so that a portion of the first column extends within the column positioning slot of the adapter support member, wherein the step of positioning the first column causes the pin switch end to be positioned in a first location; and activating the column packing apparatus so as to initiate a pressure applying step, wherein the pressure applying step applies a first pressure onto internal column components of the first column based on the first location of the pin switch end.

The method of packing a first column may further comprise placing a first column adapter on the upper surface of the adapter support member so that a first column positioning slot within the first column adapter is aligned with the column positioning slot within the adapter support member; and positioning the first column on an upper surface of the first column adapter so that a portion of the first column extends within (i)

the first column positioning slot of the first column adapter and (ii) the column positioning slot of the adapter support member.

The method of packing a first column may further comprise packing a second column, wherein the second column has an outer diameter that differs from an outer diameter of the first column. In this exemplary embodiment, the method of packing the second column comprises removing the first column adapter from the upper surface of the adapter support member; placing a second column adapter on the upper surface of the adapter support member so that a second column positioning slot within the second column adapter is aligned with the column positioning slot within the adapter support member; positioning the second column on an upper surface of the second column adapter so that a portion of the second column extends within (i) the second column positioning slot of the second column adapter and (ii) the column positioning slot of the adapter support member, wherein the step of positioning the second column causes the pin switch end to be positioned in a second location; and activating the column packing apparatus so as to initiate a second pressure applying step, wherein the second pressure applying step applies a second pressure onto internal column components of the second column based on the second location of the pin switch end, wherein the second pressure differs from the first pressure.

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . . 50%, 51%, 52% . . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims.

What is claimed is:

1. A column packing apparatus comprising:
an adapter support member having:
an upper surface,
a lower surface,
at least one sidewall extending from the upper surface to the lower surface, and a column positioning slot within said adapter support member, said column positioning slot comprising:
a slot mouth, and
a portion of the at least one sidewall, said slot mouth having a slot mouth width that is sized to accommodate a largest column width; and
a pin switch having a pin switch end that extends into (i) said column positioning slot or (ii) a volume of space directly below said column positioning slot, wherein said pin switch is operatively adapted to adjust a packing pressure of said column packing apparatus depending on a location of said pin switch end within (i) said column positioning slot or (ii) said volume of space directly below said column positioning slot.

2. The apparatus of claim 1, wherein said upper surface has a recessed area therein, said recessed area extending a depth into said upper surface and surrounding at least a portion of said column positioning slot.

3. The apparatus of claim 1, wherein said pin switch is spring-loaded so as to force said pin switch end into (i) said column positioning slot or (ii) said volume of space when in an undisturbed state.

4. The apparatus of claim 1, wherein said pin switch extends into said column positioning slot and through said at least one sidewall of said adapter support member.

5. The apparatus of claim 1, further comprising a first column adapter, said first column adapter having:
a first column adapter upper surface,
a first column adapter lower surface,
at least one first column adapter sidewall extending from the first column adapter upper surface to the first column adapter lower surface, and a first column positioning slot within said first column adapter, said first column positioning slot comprising:
a first column adapter slot mouth, and
at least one first column adapter sidewall, said first column adapter slot mouth having a first column adapter slot mouth width that is sized to accommodate a width of a first column;
wherein said first column adapter is operatively adapted to position the first column within said column positioning slot so as to cause said pin switch end to be positioned in a first location.

6. The apparatus of claim 5, further comprising a second column adapter, said second column adapter having:
a second column adapter upper surface,
a second column adapter lower surface,
at least one second column adapter sidewall extending from the second column adapter upper surface to the second column adapter lower surface, and
a second column positioning slot within said second column adapter, said second column positioning slot comprising:
a second column adapter slot mouth, and
at least one second column adapter sidewall, said second column adapter slot mouth having a second column adapter slot mouth width that is sized to accommodate a width of a second column;
wherein said second column adapter is operatively adapted to position the second column within said column positioning slot so as to cause said pin switch end to be positioned in a second location, said second location being different from said first location.

7. The apparatus of claim 1, further comprising a set of two or more column adapters, wherein each column adapter in the set has:
a column adapter upper surface,
a column adapter lower surface,
at least one column adapter sidewall extending from the column adapter upper surface to the column adapter lower surface, and
an adapter column positioning slot within each column adapter, said adapter column positioning slot comprising:

a column adapter slot mouth, and at least one column adapter sidewall, said column adapter slot mouth having a column adapter slot mouth width that is sized to accommodate a width of a spring column;

wherein said set of two or more column adapters is operatively adapted to position two or more spring columns within said column positioning slot so as to cause said pin switch end to be positioned in two or more different locations.

8. The apparatus of claim 1, further comprising a sliding member operatively adapted to engage with and disengage with a crossbar member so as to move freely along rods of a hydraulic dampening system, said rods being positioned on opposite sides of said column positioning slot, said sliding member having a connector capable of engaging with a packing adapter, said packing adapter being operatively adapted to align internal column components with a column positioned within said column positioning slot.

9. The apparatus of claim 1, wherein said crossbar member moves toward said sliding member and said column positioning slot so as to apply pressure on the internal column components.

10. The apparatus of claim 1, further comprising a hydraulic dampening system comprising an oil reservoir and tubing that connects said oil reservoir with other components of said hydraulic dampening system, wherein said oil reservoir is located at a highest point of said hydraulic dampening system.

* * * * *